United States Patent
Tian et al.

(10) Patent No.: US 9,410,970 B2
(45) Date of Patent: *Aug. 9, 2016

(54) CELLARIUM: THIN-FILM SENSOR WITH MICROARRAY SEAL

(71) Applicant: ARIZONA BOARD OF REGENTS ON BEHALF OF ARIZONA STATE UNIVERSITY, Scottsdale, AZ (US)

(72) Inventors: Yanqing Tian, Tempe, AZ (US); Liqiang Zhang, Chandler, AZ (US); Fengyu Su, Tempe, AZ (US); Deirdre Meldrum, Phoenix, AZ (US); Sean Buizer, Tempe, AZ (US); Clifford L. Anderson, Tempe, AZ (US); Laimonas Kelbauskas, Gilbert, AZ (US); Kristen Lee, Mesa, AZ (US)

(73) Assignee: ARIZONA BOARD OF REGENTS ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/533,349

(22) Filed: Nov. 5, 2014

(65) Prior Publication Data

US 2015/0126404 A1     May 7, 2015

Related U.S. Application Data

(63) Continuation-in-part of application No. 14/197,422, filed on Mar. 5, 2014, now abandoned.

(60) Provisional application No. 61/900,870, filed on Nov. 6, 2013.

(51) Int. Cl.
    *G01N 33/84*     (2006.01)
    *G01N 33/66*     (2006.01)
    *G01N 21/64*     (2006.01)

(52) U.S. Cl.
    CPC ............ *G01N 33/84* (2013.01); *G01N 21/6428* (2013.01); *G01N 33/66* (2013.01)

(58) Field of Classification Search
    None
    See application file for complete search history.

(56) References Cited

U.S. PATENT DOCUMENTS

| | | | | |
|---|---|---|---|---|
| 7,388,110 B2* | 6/2008 | Ochiai | ................... | C07F 5/025 562/7 |
| 7,635,595 B2* | 12/2009 | Lakowicz | .............. | C07F 5/025 422/400 |
| 2013/0102024 A1* | 4/2013 | Tian et al. | ........................ | 435/34 |

OTHER PUBLICATIONS

Tian et al., Dually fluorescent sensing of pH and dissolved oxygen using a membrane made from polymerizable sensing monomers, Sensors and Actuators B 147 (2010) 714-722.*
Tian et al., A fluorescent colorimetric pH sensor and the influences of matrices on sensing performances, Sensors and Actuators B 188 (2013) 1-10.*

* cited by examiner

*Primary Examiner* — Suzanne M Noakes
*Assistant Examiner* — Stephen Chong
(74) *Attorney, Agent, or Firm* — Yakov Sidorin; Quarles & Brady LLP

(57) ABSTRACT

A triple sensor structured for simultaneous measurement of glucose, oxygen, and pH. The sensor components are in thin film states such as sensing films or membranes, with a glucose probe associated with emission of radiation in the blue part of the spectrum, an oxygen probe associated with radiation in red portion of the spectrum, and a pH probe—with a green portion of the spectrum. The optical probes are chemically grafted or immobilized in a suitable polymer matrix, alleviating the leaching of the probes from the matrix, improving the thin film sensing stability, and enabling the repeatable use of the same sensing films.

11 Claims, 6 Drawing Sheets

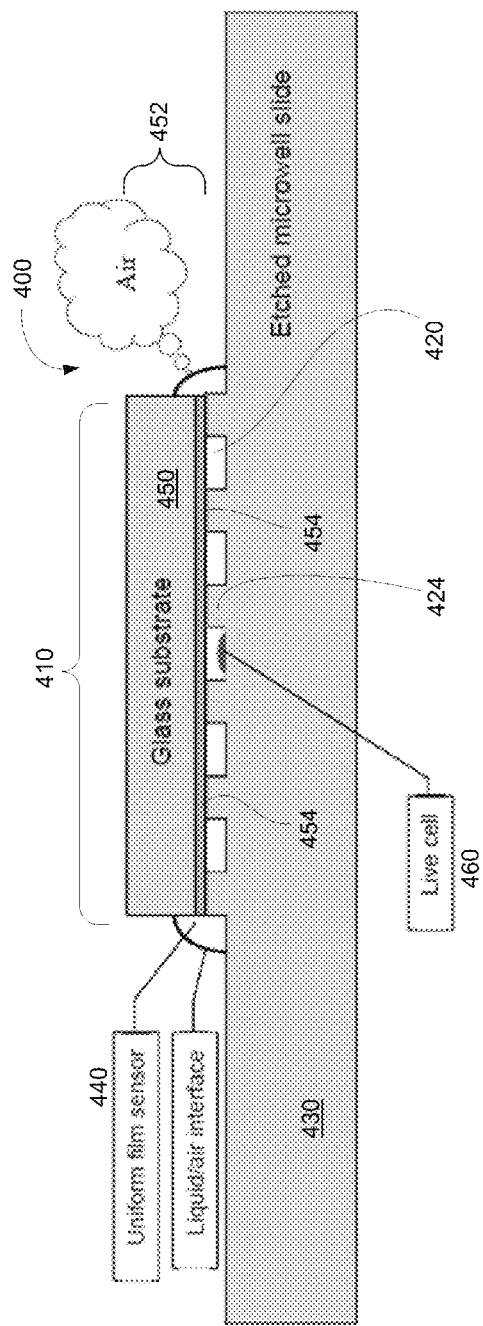
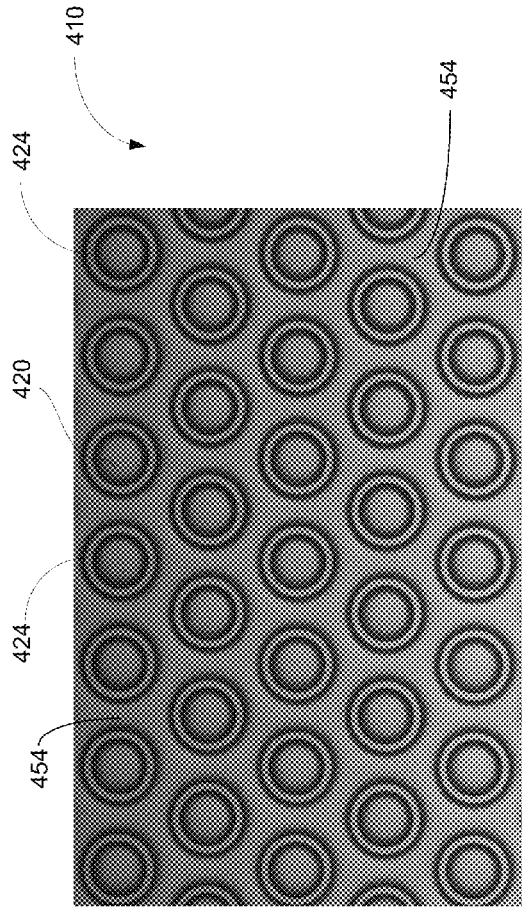
FIG. 4A
FIG. 4B

CELLARIUM: THIN-FILM SENSOR WITH MICROARRAY SEAL

CROSS-REFERENCE TO RELATED APPLICATIONS

The present application claims benefit of and priority from the U.S. Provisional Patent Application No. 61/900,870 filed on Nov. 6, 2013. The present application is also a continuation-in-part of the U.S. patent application Ser. No. 14/197,422 filed on Mar. 5, 2014. The disclosure of each of the above-mentioned patent documents is incorporated herein by reference in its entirety.

STATEMENT REGARDING FEDERALLY SPONSORED RESEARCH

This invention was made with government support under UOI CA164250 and UOI CA164250-02 awarded by the National Institute of Health. The government has certain rights in the invention.

TECHNICAL FIELD

The present invention relates to a sensor system for measuring biological parameters of tissue and, in particular, to a thin-film-based sensor system for simultaneously measuring glucose, oxygen, and pH in a sample the amount of which is below the levels required by sensors of related art to-date.

SUMMARY

Embodiments of the invention provide a sensing system containing three sensors for simultaneous measurement of glucose, oxygen, and pH. The system uses fluorescence technology in the form of optical probes which are capable of absorbing radiation and emitting light in the visible region in the form of color. For example, the sensor system includes a glucose probe, an oxygen probe, and a pH probe in a form of thin film states, referred to as sensing films or membranes, with a glucose probe (a blue light optical probe emitter which emits blue light), an oxygen probe (a red light optical probe emitter which emits red light), and a pH probe (a green light optical probe emitter which emits green light). The optical probes are chemically grafted or immobilized in a suitable polymer matrix, alleviating the leaching of the probes from the matrix, improving the sensor matrix thin film sensing stability, and enabling the repeatable use of the same sensing films. The proposed methodology can be extended to a development of a multi-sensor containing more than three sensing modalities, which may include, for example, sodium, calcium, and ATP sensors. Besides the use of fluorescence intensity for the measurements, lifetime technologies can be also applied for measurements. We believe the polymer films based new triple sensors are novel and will have significant value for biomedical and biological applications.

One embodiment of the invention provides a composition including a sensor matrix that is sensitive to at least two analytes of a sample of limited volume and that in response to interaction with said at least two analytes emits fluorescent light upon detecting at least one of the two analytes of the sample, while another embodiment describes a sensor device formed by the process including introducing a solution of at least one of a pH-probe and an oxygen-probe to a silylated surface of a substrate. The process further provides for polymerizing the solution to form a thin film sensor on the substrate and rinsing the thin film sensor.

A related embodiment provides a method of detecting an analyte including contacting a microsensor with at least two analytes from a sample of limited volume the microsensor configured to emit a fluorescent signal upon detection of at least one of the two analytes of the sample.

These and other aspects of the invention will be apparent upon reference to the following detailed description and figures. To that end, any patent and other documents cited herein are hereby incorporated by reference in their entirety.

BRIEF DESCRIPTION OF THE DRAWINGS

The invention will be more clearly understood in reference to the attached generally not to scale Drawings, of which:

FIG. 2A: oxygen plasma treatment to generate active hydroxyl groups; FIG. 2B: vapor deposition of thin TMSPMA layer; FIG. 2C: 25 μm tape used to control membrane thickness to 25 μm; FIG. 2D matrix solution dispensed onto modified quartz surface; FIG. 2E solution covered with a cover glass and polymerized at 80° C. for 1.5 h; FIG. 2F cover glass and tape removed; film rinsed using methanol; FIG. 2G the membrane was grafted with Glu-Probe in DMSO at room temperature; and FIG. 2H: sensing membrane's response to glucose. Chemicals for matrix: pH-Probe, Oxygen-Probe, AM, AHMAM, and PEGDMA. Chemicals used for grafting Glu-Probe onto the membrane: DCC, DMAP, and Glu-Prob.

FIG. 4A is a schematic diagram illustrating, in a cross-sectional view, an embodiment of a sensor of the invention including a substrate containing micro-structured wells and a well-sealing cover containing a layer with the sensor matrix.

FIG. 4B provides the top view of the central portion of the embodiment of FIG. 4A.

DETAILED DESCRIPTION

Figure 1:
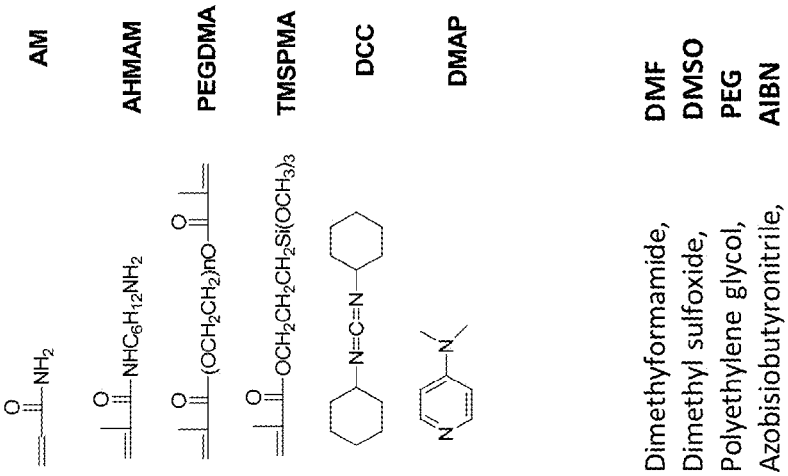
FIG. 1 illustrates the chemicals used for the sensor films preparation.
Figure 1:
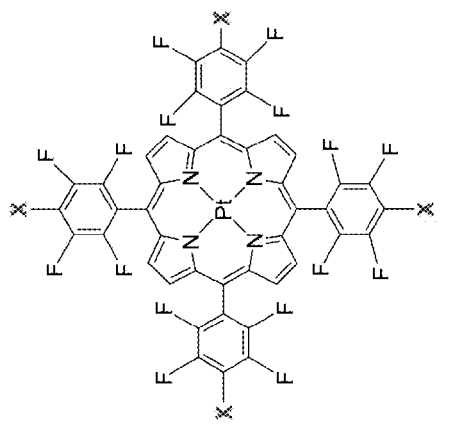
Figure 1:
Figure 1:
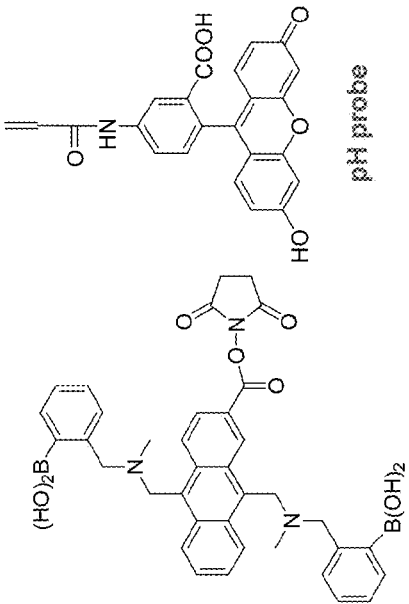

Glucose is probably the most significant energy source fueling human metabolism processes. The concentration of glucose in blood is considered to be an indicator of human health conditions, especially as an indicator relevant to diabetes. Diabetes describes a group of metabolic diseases manifested by inadequate control of glycemia. In people not afflicted with diabetes, the blood glucose concentration is usually in the range of 70 to 120 mg/dL or 4 to 8 mM. Glucose concentration becomes lower when a person is hungry and higher after a meal. In patients of diabetes, the range of glucose concentration may be much wider, from about from 30 to 500 mg/dL or from about 2 to about 30 mM. Very low glycemia, termed hypoglycemia (low blood glucose level), may lead to various detrimental outcomes including fainting and coma. Persistent or frequent hyperglycemia (high blood glucose level) may cause damage to the eyes, kidneys, nerves, and blood vessels. Currently, diabetes affects 24 million people in the US alone. It is predicted this number could increase to about 44 million by 2034 with treatment costs approaching about $336 billion. Therefore, sensors with the capacity for monitoring, especially continuously monitoring glucose, are tremendously needed. The market for glucose sensors probably is the biggest one in the diagnostic field, which is about € 30 billion per year at present.

Cellular oxygen concentration affects the cell metabolism, which describes intracellular chemical reactions that convert nutrients and endogenous molecules into energy and matter (proteins, nucleic acids, and lipids) to sustain life. Adenosine triphosphate (ATP) is the principal molecule that drives all energy-dependent cellular processes and is mainly generated by glycolysis and oxidative phosphorylation during the processes of metabolism. In glycolysis, glucose is converted to pyruvate, generating two net ATP molecules. When oxygen levels are low, anaerobic glycolysis continues, which turns pyruvate into lactate. If oxygen is plentiful, however, the process of oxidative phosphorylation occurs more efficiently, in which pyruvate is routed to the tricarboxylic acid (TCA), or Krebs, cycle in the mitochondria, generating about 36 net ATP molecules per molecule of glucose. Glycolysis process will acidify the extracellular pH.

Because of the tremendous needs for glucose sensors, after about 50 years development of glucose sensors, many glucose sensors are reported and some have been used for continuous glucose monitoring. However, sensors' sensitivities, selectivity, long-term stability, implanting applicability, and multi-functionality are not satisfactory. Further, very few dual glucose and oxygen sensors were reported either by using electrochemical mechanism or by fluorescent mechanism. There is no sensor with the capacity to measure pH, oxygen, and glucose simultaneously. Moreover, there is not a sensor that can measure limited volumes of samples. For example, for minute amounts of sample material, such as particle/sample sizes of 10 µm, 20 µm, 30 µm, 40 µm, less than 100 µm, and the like, or limited volumes such as 10 µL, 20 µL, 30 µL, 40 µL, less than 100 µL, and the like, there currently exists no sensor with the capability of measuring all three analytes within that limited volume simultaneously.

Therefore, simultaneous measurements of glucose, oxygen, and pH can provide information for glucose concentrations, oxygen concentrations, extracellular pH, the relationship among oxygen, glucose and pH, and organism's or cell's glucose metabolism under different stimulus and proliferative states. Such sensors can be useful for diabetes monitoring, for hypoxia (low oxygen) related disease diagnoses, for cancer therapeutic diagnoses, and for fundamental understanding of biological processes of the metabolism.

This invention describes a new polymer-film-based sensor system structured to be operable for simultaneous measurements of levels of glucose, pH, and oxygen in a minute quantity of a biological tissue that is shown to be insufficient for measurement using currently-available sensor systems. The system uses fluorescence technology in the form of optical probes which are capable of absorbing radiation and emitting light in the visible region in the form of color. For example, the sensor system includes a glucose probe, an oxygen probe, and a pH probe in the form of thin film states, referred to as sensing films or membranes, with a glucose probe (a blue light optical probe emitter which emits blue light), an oxygen probe (a red light optical probe emitter which emits red light), and a pH probe (a green light optical probe emitter which emits green light). In an embodiment, the optical probes are chemically grafted or immobilized in a suitable polymer matrix, alleviating the leaching of the probes from the matrix, improving the sensor matrix thin film sensing stability, and enabling the repeatable use of the same sensing films. For example, embodiments of the invention are structured to effectuate measurements of glucose, pH, and oxygen concentrations in aqueous solutions, including measurements in a complicated biological environment. Although many individual optical sensors for glucose, pH, and oxygen were developed and used for bioapplications, conventional sensors used to-date are usually employed for detection of a single analyte or two analytes and none has been demonstrated for simultaneous determination of three analytes. This tri-sensor which combines three probes together on one sensing film makes it capable to detect glucose, oxygen and pH simultaneously by one device to provide the correlation of the three biological parameters simultaneously with the highest spatial and temporal resolution.

The consumption rate of glucose and oxygen, combined with the change of pH, are three major metabolic parameters to monitor physiological response to physical training, exercise, disease and treatment. These are also the major parameters in research to detect a cell's metabolic responses to stress and proliferative status, such as cancerization, inflammation and wound healing. Due to the importance of these biological parameters both in research and clinical setting, a lot of effort has been dedicated to development of probes and/or devices for determination of these parameters glucose, oxygen and pH. Until now, however, not a single implementation of such a device facilitates the simultaneous detection of these three parameters simultaneously.

The idea of the invention stems from the realization that a tri-sensor (which combines three probes together on one sensing film) is operable to detect glucose, oxygen and pH simultaneously in one measurement cycle to provide the correlation among the three biological parameters simultaneously with the highest spatial and temporal resolution. In contradistinction with sensors of related art, the use of which understandably begs a question of which experimental errors are or are not present during the independent and uncorrelated measurements of glucose, oxygen and pH with independent sensors, the proposed integrated solution allows for determination of the sought after levels in a single measurement cycle with the very same device and, at least for this reason, provides for optimally-determined correlation among the resulting data. Embodiments can be employed for continuous measurement of glucose for monitoring diabetes and can be used for understanding and/or monitoring cell metabolism under different circumstances, such as proliferation, inflammation, and low oxygenation (hypoxia).

As shown in the discussed-below examples of a device, because the sensor film is prepared using a polymerization approach (such as, for example, thermal polymerization, photopolymerization, and/or chemically oxidative polymerization), a particular sensor device can be layered on substrates such as glass and/or plastic, or polyethylene terephthalate (PET). The shapes, sizes, and dimensions of the sensor are generally variable and controllable during the process of fabrication. In an embodiment, sample/particle size may be substantially similar to the size of the sensor. For example, sizes of the sensor may include about 10 µm, about 20 µm, about 30 µm, about 40 µm, less than 100 µm, and the like, for sensing sample or particle sizes of about 10 µm, about 20 µm, about 30 µm, about 40 µm, less than 100 µm, and the like. Further, the sensor is capable of determining simultaneous measurements of levels of glucose, pH, and oxygen in a minute limited quantity of a biological sample having volumes such as about 10 µL, about 20 µL, about 30 µL, about 40 µL, less than 100 µL, and the like. In an embodiment, a given implementation of the sensor of the invention can be a microsensor placed in a single-cell study microwell (with a typical diameter of about 80 µm and a height of about 20 µm, corresponding to a sample volume of about a single cell) for studying single-cell respiration and metabolism. Of course, in related implementations, the area of a sensor film size can also be substantially larger, for example a few square millimeters, centimeters or even as large as 100 cm². It is also within the scope of the invention to place the integrated sensor in a microfluidic device and/or a host device that is implantable into a biological tissue for long term blood glucose and oxygen monitoring.

EXAMPLE 1

1.1 Materials and Reagents

All chemicals and solvents were ordered from suppliers with analytical grade and were used without further purification. Glucose, methanol, N,N'-dimethylformamide (DMF), dimethyl sulfoxide (DMSO), N-hydroxysuccinimide (NHS), 4-dimethylaminopyridine (DMAP), N,N'-dicyclohexylcarbodiimide (DCC), 3-(trimethoxysilyl)propyl acrylate (TMSPA), and monomers for matrix including 2-hydroxyethyl methacrylate (HEMA), acrylamide (AM), poly(ethylene glycol) dimethacrylate (PEGDMA, Mn=550), and azobisisobutyronitrile (AIBN) were commercially available from Sigma-Aldrich (St. Louis, Mo.).

Oxygen probe (OS2), glucose probe (Glu-probe) and pH probe shown in FIG. 1 were prepared according to procedures known to those of skill in the art. 6-Aminohexyl methacrylamide (AHMAM) was synthesized according to a modified procedure known to those of skill in the art. The pH values were determined with a digital pH meter (Thermo Electron Corporation, Beverly, Mass.) calibrated at room temperature with standard buffers. Percentages of oxygen (0-100) were tuned by the instrument designed by ourselves. For fluorescence measurements, quartz glasses from University Wafer (South Boston, Mass.) were cut into squares of 13 mm×13 mm using a dicing saw (Microautomation, Billerica, Mass.).

1.2 Instruments

MALDI-TOF mass spectrometry was performed by the ASU Mass Spectrometry Laboratory. A Varian liquid-state NMR operated at 300 MHz for 1H NMR was used for NMR spectra measurements. An oxygen plasma cleaner (Harrick Plasma, Ithaca, N.Y.) was used for quartz glass surface activation. A Shimadzu RF-5301 spectrofluorophotometer was used for fluorescence measurements. For easy measurement of the films in liquid solutions, quartz glass was cut with a dicing saw into squares of 13 mm×13 mm, which can fit diagonally into a quartz fluorescence cuvette to enable the sensing membrane be positioned at an angle of 45° to the excitation light.

1.3 Preparation of Sensing Film

The sensor film with probes immobilized in the matrices were prepared using the protocol described in the schematic drawing given in FIG. 2.

1.3.1 Quartz Substrate Salinization.

Figures 2A, 2B, 2C, 2D, 2E, 2F, 2G, 2H:
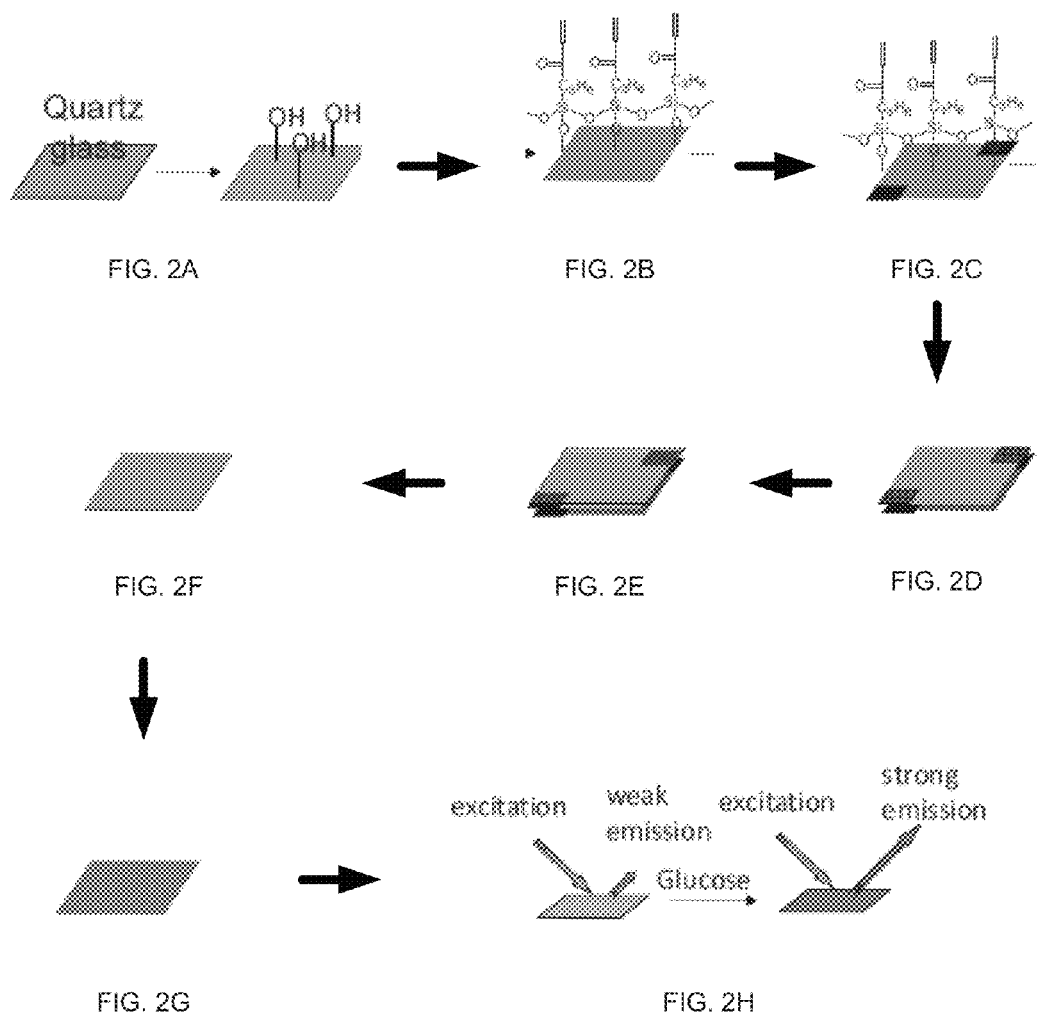
FIGS. 2A, 2B, 2C, 2D, 2E, 2F, 2G, and 2H depict schematically the preparation of sensing membranes.

To achieve stable polymer membranes on the quartz glasses, the surface of quartz substrate was modified with TMSPA. Detergent and acetone-cleaned quartz glass was treated with oxygen plasma for 45 min to generate active hydroxyl groups (FIG. 2a). Immediately following plasma treatment, the quartz glass was placed in a vacuum desiccator to graft a thin layer of TMSPA on its surface under vacuum for 20 h using a known vapor deposition approach (FIG. 2b).

1.3.2 Preparation of Sensor Films

Typical probe structures and other chemicals used for the sensing film matrix preparation were given in FIG. 1. In a typical example, 100 mg of the AHMAM, 1000 mg of AM, 50 mg of PEG dimethacrylate (PEGDMA), 1 mg of the pH probe, 10 mg of the oxygen probe, and 10 mg of AIBN were dissolved in 1 mL DMF as the stock solution for thin film preparation. 10 μL of the stock solutions were added onto the surface of the TMSPA-modified quartz glass and covered with a clean but untreated cover slip to make a sandwich structure (FIGS. 2c, 2d, 2e). The quartz glass was modified using TMSPA to enable the chemical grafting of the sensors and matrices onto the quartz substrate. To produce the polymer thin film with good mechanical stability, PEGDMA was used as a cross-linker. The crosslinkers can also be ethoxylated (3) trimethylolpropane triacrylate (SR454) or N,N'-ethylenebis(acrylamide). The thickness was controlled using 25 μm KAPTON film (DUPONT, Wilmington, Del.) (FIG. 2c) providing a thin film thickness of the triple sensor of about 25 p.m. The sandwich set-up was placed into a vacuum oven, which was then evacuated and refilled with nitrogen three times. Polymerization was carried out under nitrogen at 80° C. for 1.5 hours in the oven. The quartz glasses with polymer membranes were removed from the oven, with KAPTON film and non-surface modified glass being removed from the polymerized membrane surface. The polymer membranes (FIG. 2f) on the quartz glasses were washed three times using methanol to remove any remaining non-polymerized monomers and residual DMF. The films were dried and then immersed in Glu-Probe-containing DMSO solution with DCC and DMAP to graft the Glu-Probes onto the sensing films (FIG. 2g). After a 16 h long reaction, the films were taken out of the Glu-Probe-containing DMSO solution with DCC and DMAP and washed with methanol a few times and then DI water, dried and stored in the dark at room temperature. The method provides a sensor that is a composite material of Glu-Probe, pH-Probe, and oxygen probe in a matrix of AM, AHMAM, PEGDMA, and TMSPMA. FIG. 2h illustrates sensing membrane's response to glucose.

1.4 Sensor Characterization

The quartz glass with sensing film was positioned with a 45° facing angle to the excitation light in a spectrofluorophotometer. To test the response of the triple sensor to glucose, the triple sensor was incubated in PBS buffer containing a specific concentration of glucose for 1 minute at room temperature before it was tested for the fluorescent response with 390 nm as excitation wavelength. The emissions were collected from 410 nm to 700 nm. The response to oxygen was tested in PBS buffer containing 5 mM of glucose. The dissolved oxygen in solution were tuned from 0 mg/L to 41 mg/L, corresponding to oxygen partial pressure of 0% to 100% of atmospheric pressure by bubbling gas oxygen/nitrogen into the liquid for 2 minutes at each step. The triple sensor was also excited by 390 nm to test the fluorescent response to oxygen with the spectra from 410 n m to 700 nm. Buffers with specific pH containing 5 mM of glucose were used to test the triple sensor response to pH. After incubation in each pH buffer for 30 seconds, 488 nm was applied to excite the triple sensor. The emissions were collected from 500 nm to 700 nm. Limited volumes used for testing the fluorescent response of the triple sensor can include less than 10 μL, less than 20 μL, less than 30 μL, less than 50 μL, and less than 100 μL.

Figure 3A:
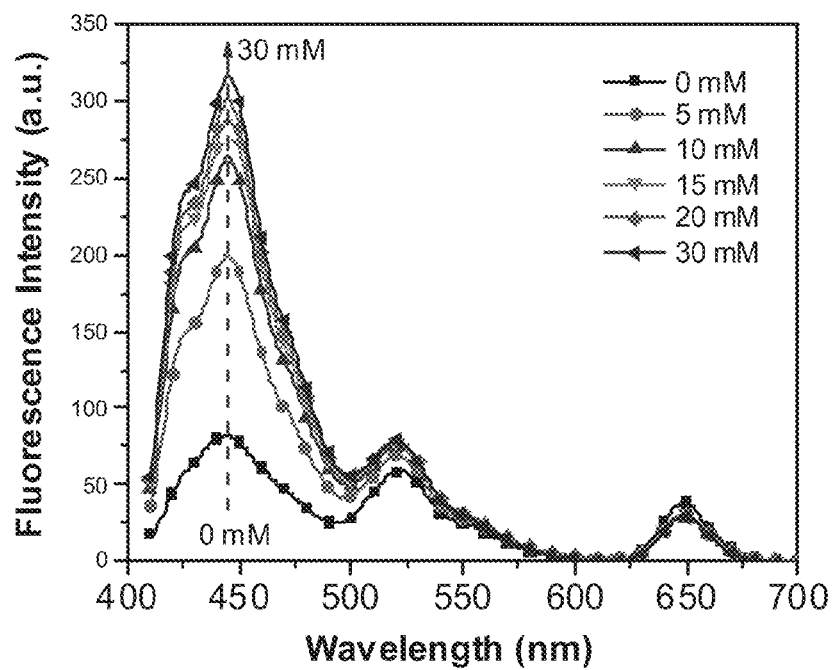
FIG. 3A depicts responses to glucose under an excitation at 390 nm.
Figure 3B:
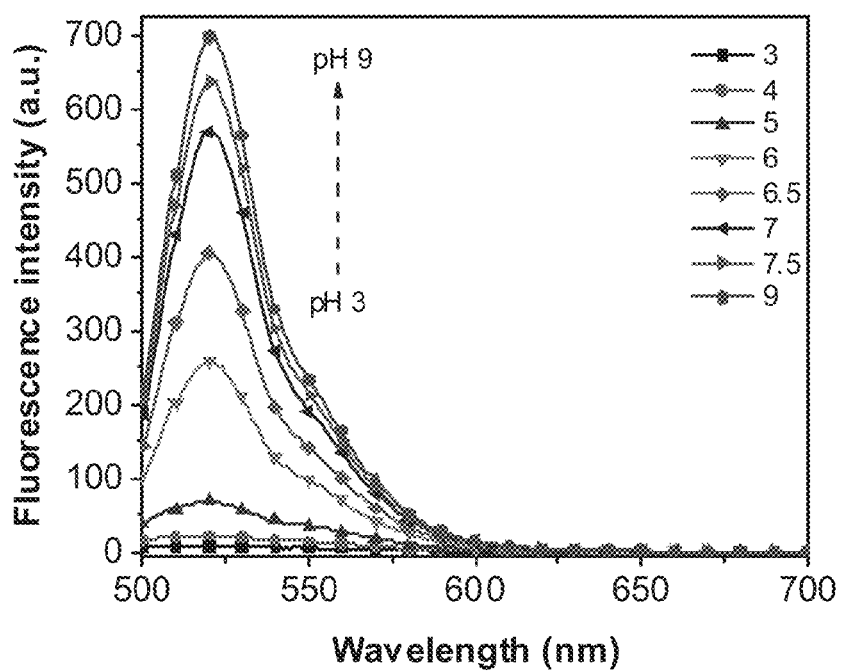
FIG. 3B depicts responses to pH under the excitation at 488 nm.
Figure 3C:
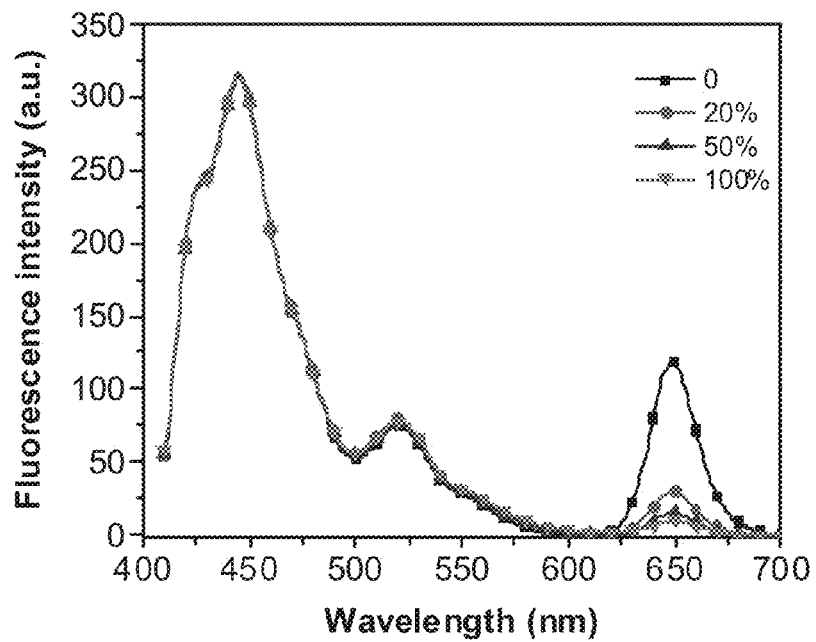
FIG. 3C depicts responses to oxygen under the excitation at 390 nm.
Figure 3D:
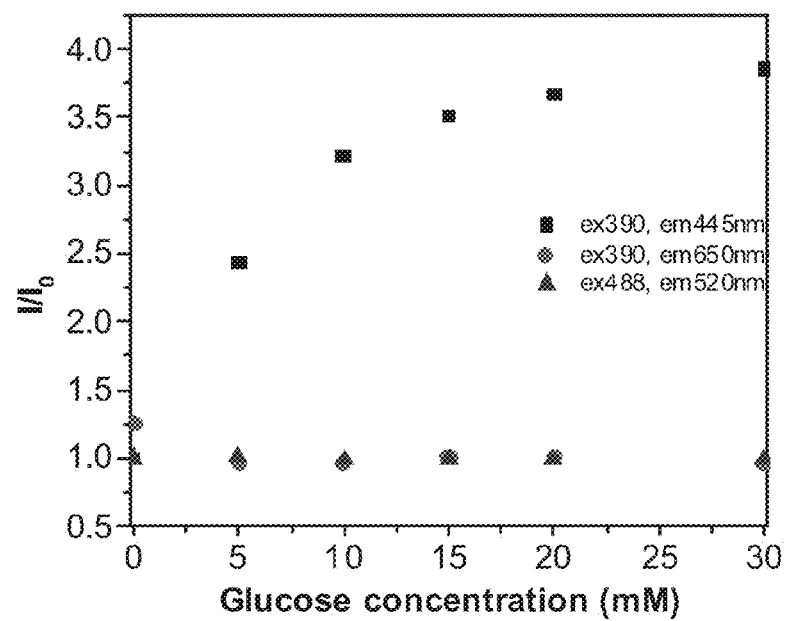
FIGS. 3D, 3E, and 3F illustrate intensity ratios via the analytes. $I_0$ in FIG. 3D is the intensity without glucose. $I_{pH=3}$ in FIG. 3E is the intensity at pH 3. $I_0$ in FIG. 3F is the intensity under nitrogen.
Figure 3E:
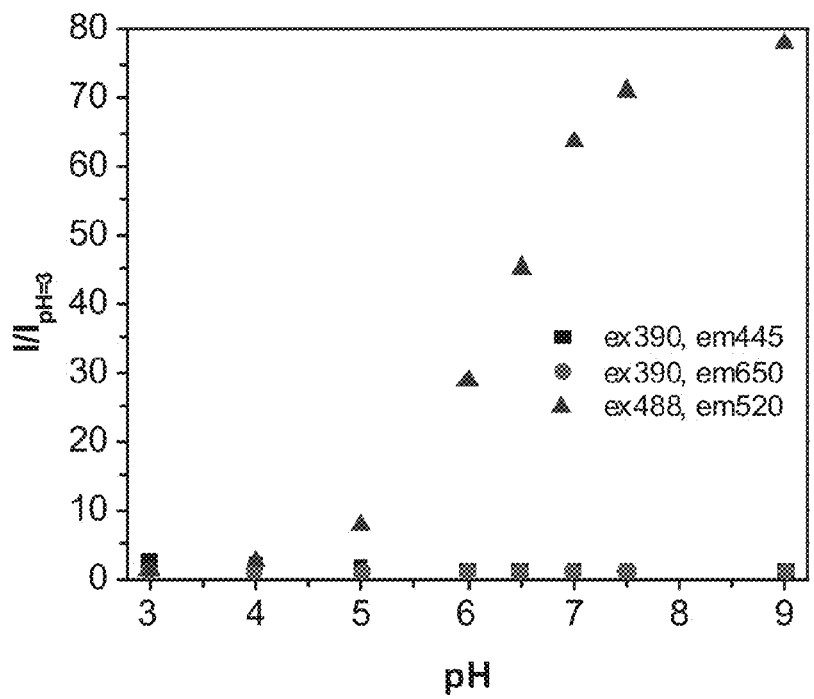
Figure 3F:
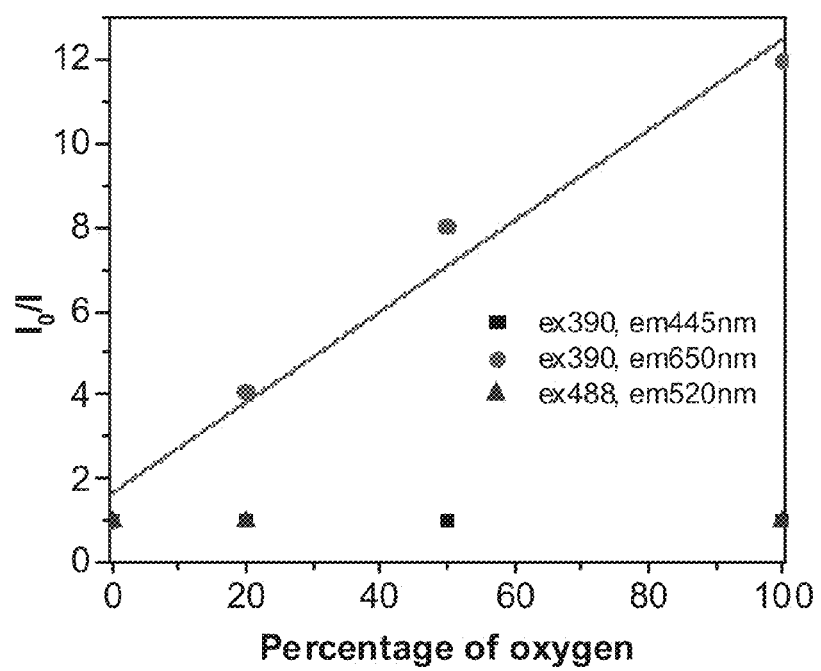

FIG. 3A shows the triple sensor's response to glucose. The emission intensity increases with increasing glucose concentration (FIGS. 3A and 3D). The sensor can be used for glucose measurement from about 1 mM to about 20 mM, indicating it will be suitable for biological studies as well as for diabetes diagnosis. It was noted from FIG. 3D, the emissions from the oxygen probe and the pH probe did not change significantly by glucose, demonstrating that there is no cross-talk of the probes. FIG. 3B shows the pH responses under an excitation at 488 nm. FIG. 3E plots the intensity changes for all three probes under different pH values. It was found that glucose and oxygen probes are not affected significantly by pH. The triple sensor can respond to pH conditions exhibiting a pH value from about pH 5 to about pH 7.5, indicating its suitableness for biological pH applications (generally about pH 7.3). FIG. 3C shows the sensor responses to oxygen under an excitation wavelength of 390 nm. The glucose and oxygen probes were not affected by the presence of oxygen during sensor characterization (FIG. 3F). The sensor is suitable for the measurement of substantially all dissolved concentration ranges.

A more general implementation of the invention may be structured to facilitate the analysis of living cells, for example as part of a chamber device for analyzing living cells, and include a base and a lid that, when reversibly pressed closed to one another, form a seal therebetween and where the base is configured to contain an optically transparent microwell dimensioned to house at least one cell. The lid may have a thin, sensor coating defining one or more sensor elements that pass(es) through the chamber seal. A sensor coating is made at a thickness about 1 micron by fabricating a 1 micron shim using a photolithographically patterned photoresist on a substrate, where the shim is aligned along two or more edges of the substrate allowing the sensor to be filled in its interior area while controlling thickness of the sensor. Such sensing structure may be used to implement a method for performing phenotypic measurements of at least one cell in the microwell where, in order to assess the state of the seal of the chamber, a chosen gas concentration is measured both inside and outside the microwell in order to determine leakage characteristics of such chosen gas. The gas may include a known amount of oxygen and be applied to the perimeter of the chamber after cellular respiration data are collected sufficient to effectuate compensation of oxygen leakage through the seal. One or more sensor elements in the chamber can be patterned in such a manner as to expose multiple sensor elements that traverse the seal to the well interior and exterior without requiring precise mechanical alignment. In a specific implementation, one or more sensor elements may include three sensor elements structured to have thickness and mechanical compliance sufficient to accommodate small foreign material and variation in both substrate and a surface of the sensor element(s) finish while still enabling a sealable connection between the base and the lid. Such compliance may be defined in addition to compliance provided by the well substrate.

In a process of performing a phenotypic measurement, cell(s) can seeded in a microwell and excluded from outside the microwell, both on the seal area and other areas, by transverse liquid flow. The cell seeding technique may include a specific step of removal of unwanted cells with a flow of a thin film of cell medium or PBS subject to gravity forces.

EXAMPLE 2

In reference to FIGS. 4A and 4B, an embodiment of the sensor device is disclosed, which device is used for analyzing live single cells or cell-clusters with the use of fluorescence-based sensors as discussed above. An operating chamber 410 of the device 400 includes cylindrically-shaped microwells/chambers 420 with diameters starting on the order of 60 micron to larger diameters of 1 to 3 millimeters (in one example: 2.8 mm). Each of the wells has a lip 424 defining the corresponding well perimeter, which lip is raised above the surface of the well-carrying substrate 430. The key element of this embodiment is the combination of a uniformly-deposited sensory component (matrix) 440 on a flat support 450, aggregately forming the sealing cover above the array of chambers 420, where the sensory component 440 is formed along the surface of the sealing cover 450 in a continuous fashion. In practice, the sensory component is deposited via the processes of casting or spin coating, on a rigid, low-permeability support 450 such as fused silica. The support 450 has a thickness from about 0.2 μm to about 25 μm, and preferably in the range from about 0.4 μm to about 5 μm. The contraption 452 containing the support 450 with the sensory component 420 thereon is then "flipped over" to cover the well-array in a sealing fashion to fluidly (and, optionally, hermetically) seal the contents of wells 420 therein. It is understood that portions 454 of the sensory component 440 end up outside a well and in-between individual wells, thereby providing an advantage of positively control the quality of the sealing contraption 452, as well as an opportunity to negatively control respiration of live-cell(s) sealed within the individual well 420.

The sensor film 440 does not need to be patterned or deposited into individual wells. The proposed elimination of patterning facilitates not only much lower costs of the processing of the sensor film but also much more uniform properties of the resulting sensor device. The elimination of patterning also greatly simplifies the mechanical assembly process by not requiring precise alignment. As a result of the configuring the sensory component as a spatially-continuous thin-film 440, the sensor covers the entire well area, thereby eliminating the non-sensor ("keep-out") areas present in patterned sensors that is required to accommodate alignment tolerances. We unexpectedly discovered that, in operation, spatially-continuous structuring of the sensory component leads to better signal-to-noise ratio. Another benefit of the non-patterned sensor is that sensor portions 454 outside individual wells (interstitial areas, positioned above the well-lips 424) is consistent in response with respect to sensor inside a well 420 for identical conditions both in terms of intensity at a given analyte value and in terms of the ratio of response for two known analyte values.

It is appreciated that, with the use of the embodiment 400, the acquisition and/or characterization of the respiration of the cell(s) 460 in an individual well 420 can be effectuated. Specifically, data representing gas (such as oxygen, for example) or gas mixture emanating from under the seal 452 from the sealed well 420 at the periphery of the microarray after sufficient cellular respiration (for example, after 15 to 60 minutes after the living cell(s) were placed into the wells) data has been collected (typically 15 to 60 minutes) can be collected in order to assess the seal performance (leak detection) in situ, while the cells are still in the wells and either consuming oxygen or not. Such detection is preferably configured without making changes to the configuration of the seal contraption 452.

It is appreciated that, when the seal formed over the wells 420 with the use of contraption 452 has high quality, the change of analyte(s) inside the well(s) 420 due to cell metabolism does not affect the ambient environment corresponding to the interstitial regions of the sensor 400. Accordingly, any change in response measured at the interstitial region may be attributed to leakage of analyte from or to neighboring wells 420. Although analytes in the interstitial area will diffuse to or from the perimeter of the well-microarray subject to a gradient thus reducing the response, a leak of sufficient magnitude can be detected given that It would be appreciated that the use of the embodiment 400 is facilitated by randomly seeding the cells 460 to minimize or eliminate cells in the interstitial areas (corresponding to portions 454 of the sensory component 440) and on the well lips using trapping of cells in the wells. After seeding cells 430 onto the substrate following protocol known to those skilled in the art, and after waiting a short period such as 10 minutes to ensure an adequate number of cells have entered wells, but not necessarily attached to surfaces, the substrate is tipped at an angle of preferably between 5 and 15 degrees in order to allow cells on the well lips and in the interstitial areas to flow off of the well-microarray. The angle is selected to create enough velocity to encourage cells to move along unless they are trapped in the open wells. After, the wells with the cells 460 inside at least some of the wells are sealed with the sealing contraption 452.

In a related embodiment, a combination of pH, oxygen and glucose, or other analyte sensor, into a thin film which does not require and is devoid of patterning (thereby simplifying the alignment of such sensory component with the array of microwells) is used for construction of a sensor device of the invention.

It is understood that the scope of the invention and materials and methods are not intended to be limited to the specific embodiments and examples described herein.

What is claimed is:

1. A composition comprising:
a sensor matrix containing first, second, and third probes at least one of which has formula I:

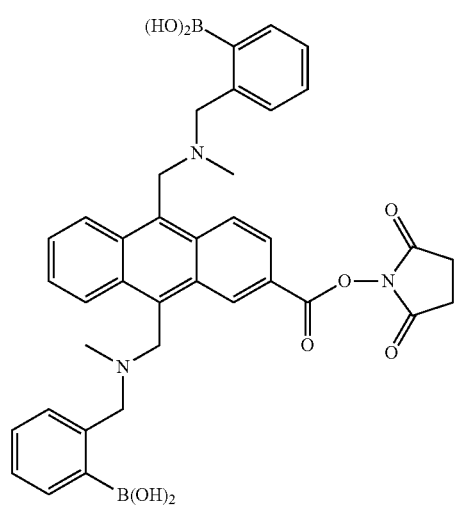

said sensor matrix configured to generate light in response to simultaneous interaction with at least three analytes of a sample of limited volume, said sensor matrix
wherein said first probe is configured to emit, in response to interaction with and detection of only first analyte from the at least three analytes, first flourescent light;
wherein said second probe is configured to emit, in response to interaction with and detection of only second analyte from the at least three analytes, second flourescent light;
wherein said third probe is configured to emit, in response to interaction with and detection of only third analyte from the at least three analytes, third flourescent light.

2. The composition of claim 1, wherein the limited volume comprises less than 30 μl.

3. The composition of claim 1, wherein the limited volume comprises a single cell.

4. The composition of claim 1, wherein the limited volume comprises less than 20 microliters.

5. The composition of claim 1, wherein the at least three analytes of the sample comprise pH, oxygen, and glucose.

6. The composition of claim 1, wherein the sensor matrix comprises a composite of at least three members of the group consisting of a glucose-probe, a pH-probe, an oxygen-probe, acrylamide, aminohexyl methacrylamide, poly(ethylene glycol) dimethacrylate, and 3-(trimethoxysilyl)propyl methacrylate.

7. The composition of claim 6, wherein a probe from said first, second, and third probes that has said formula I is a glucose-probe.

8. The composition of claim 1, wherein at least one of the first, second, and third probes has a formula II:

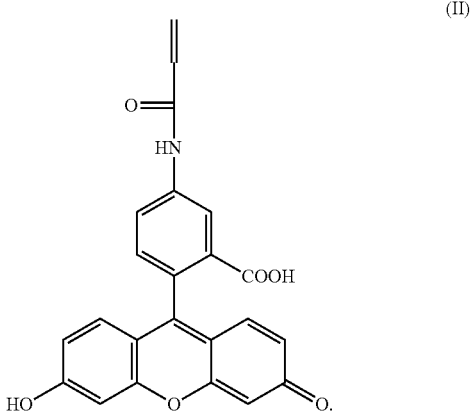 [SMILES: C=CC(=O)Nc1ccc(-c2c3ccc(=O)cc-3oc3cc(O)ccc23)c(C(=O)O)c1]

9. The composition of claim 1, wherein at least one of the first, second, and third probes has a formula III:

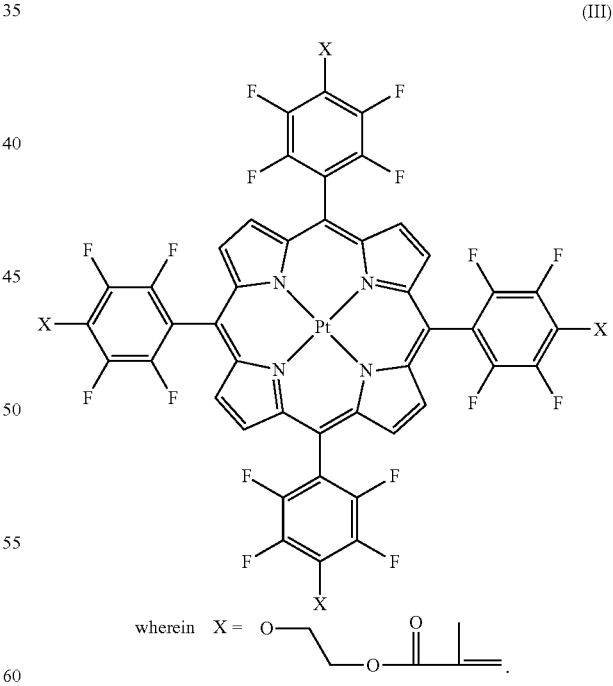

10. The composition of claim 1, wherein a probe from said first, second, and third probes that has said formula I is configured to emit, in response to interaction with and detection of a respectively-corresponding analyte from the at least three analytes, the first fluorescent light having a first wavelength in a blue region of optical spectrum.

11. The composition of claim 10, wherein a highest peak of spectral distribution of intensity of said first fluorescent light is at a wavelength between 500 nm and 550 nm.

\* \* \* \* \*